US00PP32964P3

(12) United States Plant Patent
Maillard et al.

(10) Patent No.: US PP32,964 P3
(45) Date of Patent: Apr. 13, 2021

(54) APPLE TREE NAMED 'BABYLOVE'

(50) Latin Name: ***Malus domestica* Borkh.**
Varietal Denomination: BABYLOVE

(71) Applicant: AGRO SELECTIONS FRUITS, Elne (FR)

(72) Inventors: Laurence Maillard, Elne (FR); Arsène Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 110 days.

(21) Appl. No.: 16/602,676

(22) Filed: Nov. 20, 2019

(65) Prior Publication Data

US 2020/0178433 P1 Jun. 4, 2020

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Anne Marie Grunberg
(74) *Attorney, Agent, or Firm* — Birch, Stewart, Kolasch & Birch, LLP

(57) ABSTRACT

A new and distinct variety of apple tree denominated 'BABYLOVE' produces high yield of fruits with small to very small size and round flattened shape, an orange red to red skin color, firm to very firm, and with exceptional eating quality; the fruit is further characterized by its good handling and storage qualities.

3 Drawing Sheets

This application claims priority of Community plant variety right No. 2018/3122 filed on Nov. 29, 2018 which is hereby incorporated by reference in its entirety.

Latin name of the genus and species of the plant claimed: *Malus domestica* Borkh.

Variety denomination: 'BABYLOVE'.

BACKGROUND OF THE NEW VARIETY

Field of the Invention

In the field of plant genetics, we conduct an extensive and continuing plant-breeding program including the organization and reproduction of orchard trees, among which apple, peaches, nectarines, apricots, and cherries are exemplary. It was against this background of our activities that the present variety of apple tree was originated and reproduced by us in our experimental orchard located near Elne, Pyrénées Orientales, France.

ORIGIN OF THE VARIETY

The present invention relates to a new a distinct variety of apple tree *Malus domestica* Borkh. which has been given the variety denomination 'BABYLOVE'. This tree produces fruits with a long shelf life without alteration after harvesting, very good eating quality with a white flesh for fresh market in October in the Pyrénées Orientales department, France. Contrast is made to 'REGALYOU' apple tree variety (U.S. Plant Pat. No. 25,827) for reliable description. 'BABYLOVE' is a promising candidate for commercial success in that it produces very attractive fruits having a long shelf life.

The present new variety of apple tree (*Malus domestica* Borkh.) was developed by us in our experimental orchard located in France. 'BABYLOVE' apple tree originated in a cultivated area of the South of France, in the Pyrénées-Orientales department where it was also tested. This zone also called Roussillon is subject to a Mediterranean climate. The winter is generally sweet and the summer is hot and dry. The total amount of cold hours lower than 7° C. (Celsius) varies from 700 hours to 1200 hours. The total amount of sunshine hours is an average of 2400 hours to 2800 hours per year. The prevailing wind is called "Tramontane": it dries the air and clear the sky from cloud but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen and the summer is dry with a few thunderstorms.

The 'BABYLOVE' variety results from an open pollination of the apple tree variety named 'REGALYOU' (U.S. Plant Pat. No. 25,827) which was used as the seed parent. Thus, the pollen parent is unknown.

The 'BABYLOVE' variety was obtained by hybridizing and propagated by grafting on a 'M9EMLA' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

SUMMARY OF THE NEW VARIETY

The new variety 'BABYLOVE' produces fruits of small to very small size, firm to very firm and crunchy, and with a luminous orange red to red color. The blooming period is medium for the variety, namely at the end of March or in April. The maturity period is considered very late, during October in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
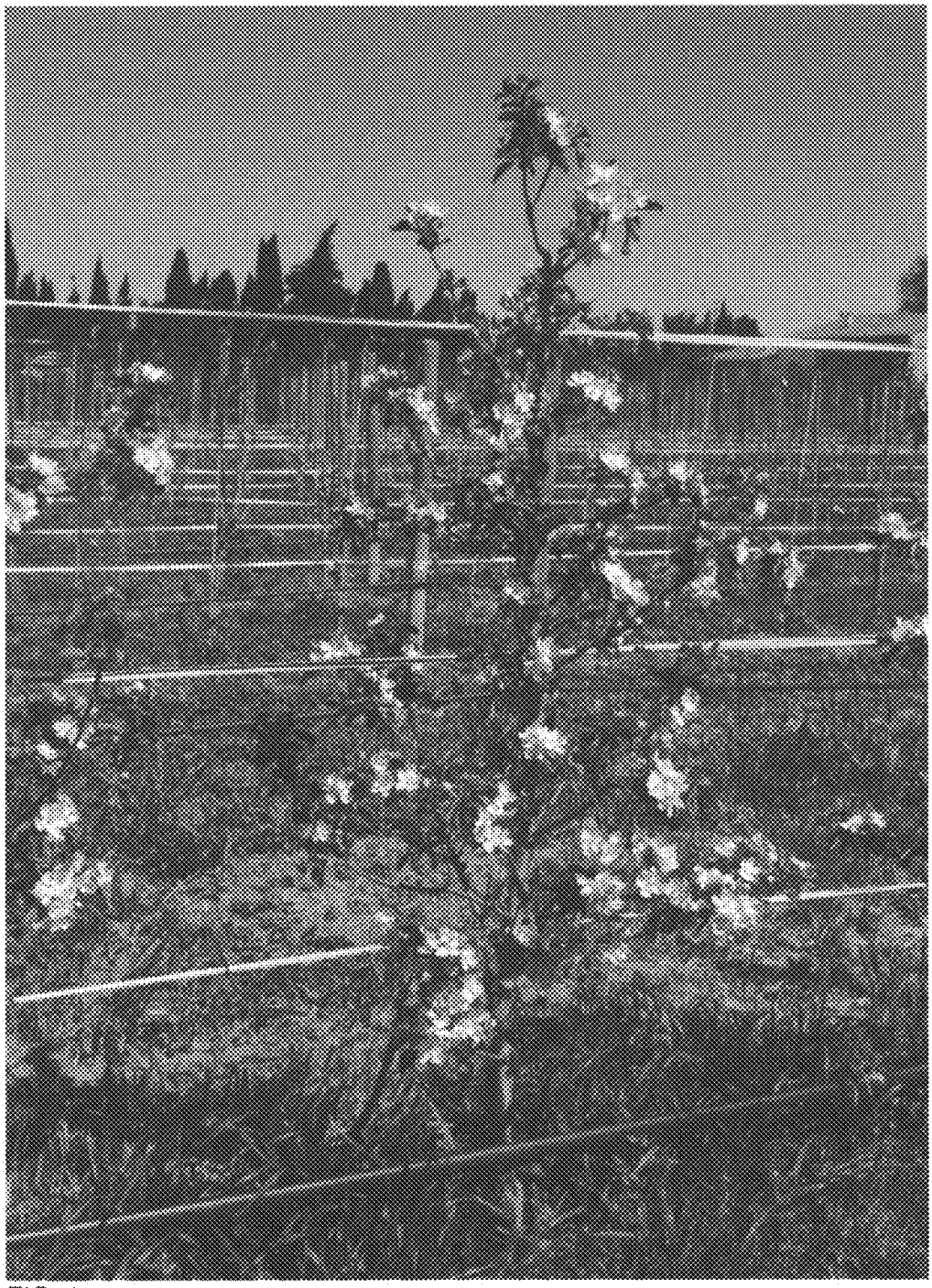
FIG. 1 is a color photograph which shows a tree of the new variety in orchard at blooming time.
Figure 2:
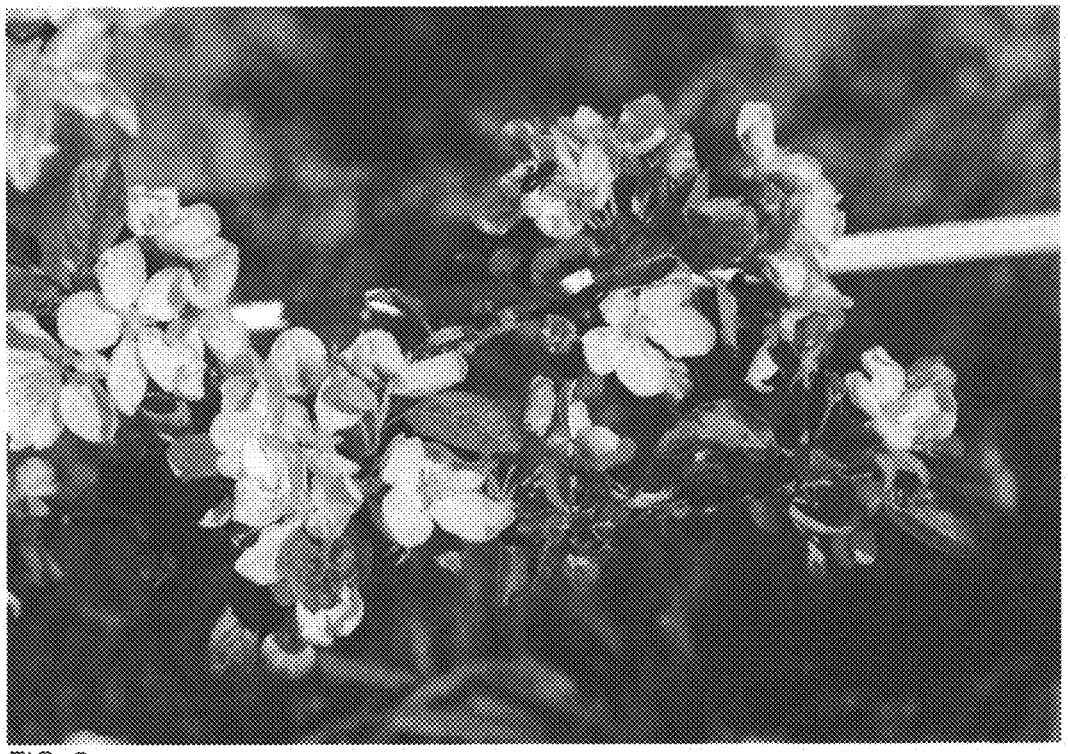
FIG. 2 is a close view of a branch of a tree of the new variety in orchard at blooming time, with open flowers and some flower buds still closed, for depicting the flower buds at different stages of development, and leaves of the new variety.
Figure 3:
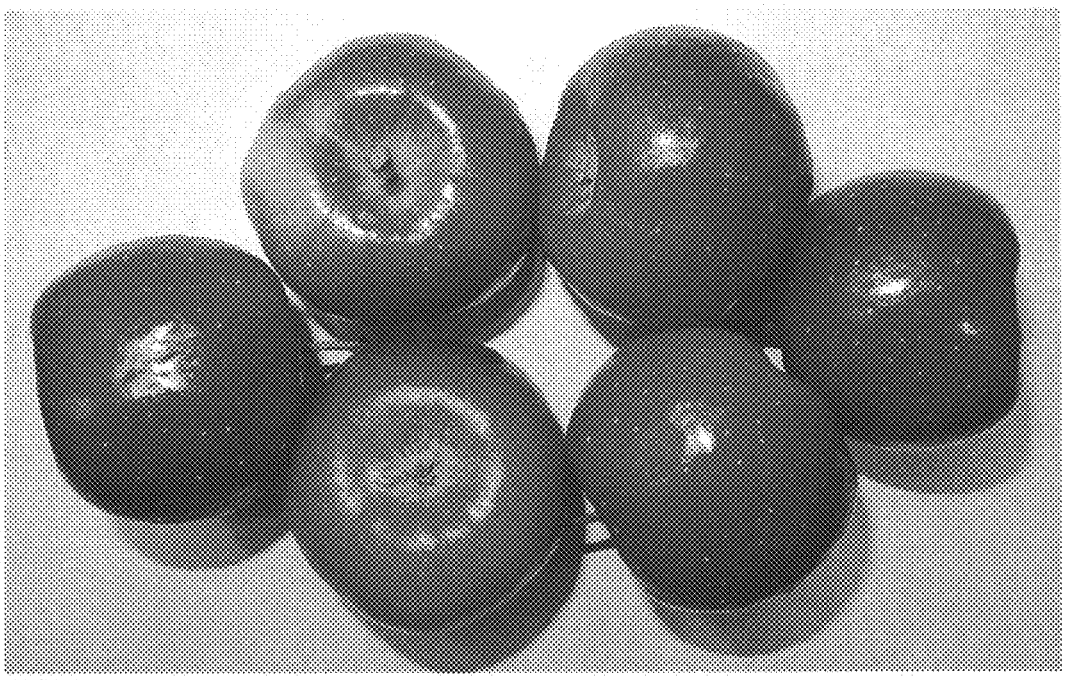
FIG. 3 is a color photograph that shows different views of six typical fruits of the new variety 'BABYLOVE' at ripening time.
Figure 4:
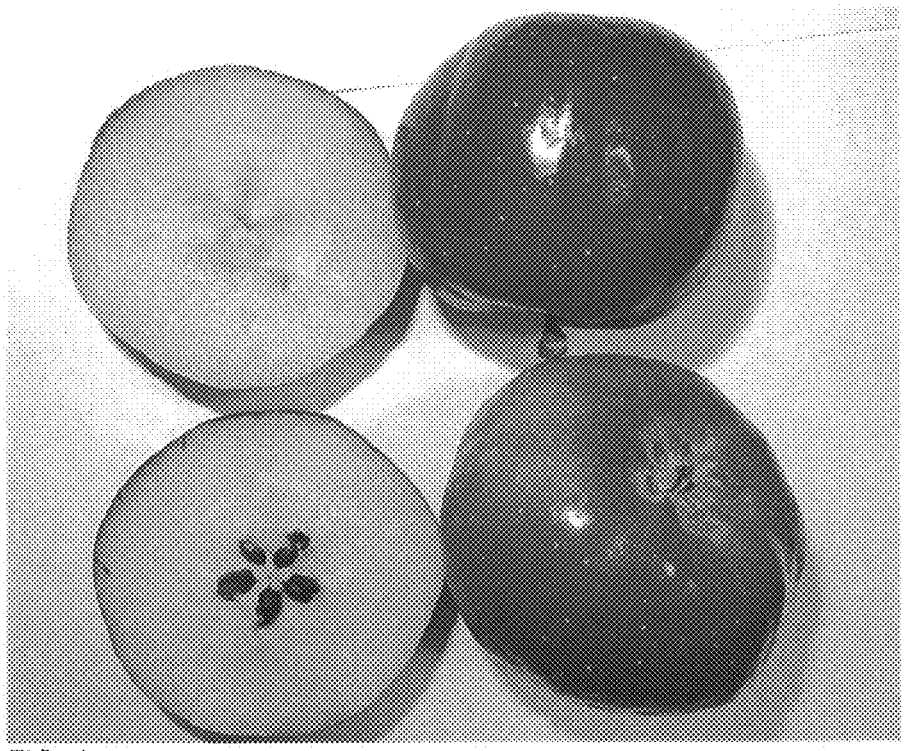
FIG. 4 is a color photograph which shows two whole fruits of the new variety at ripening time, and a third fruit, cut in a half in transverse cross section for depicting the fruit flesh, the seeds and the locules of the new variety.
Figure 5:
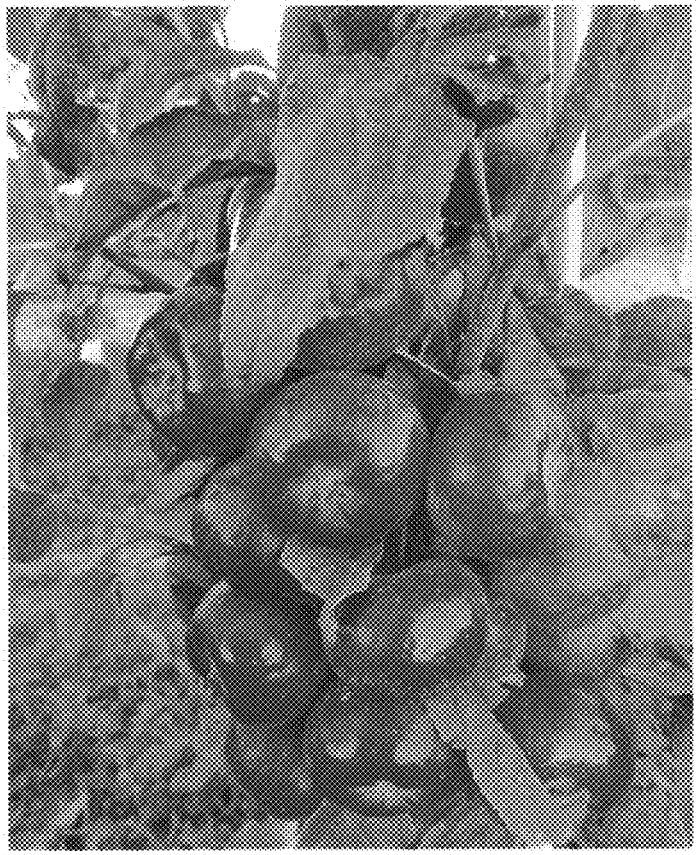
FIG. 5 shows a branch of a tree of the new variety in orchard, at ripening time, bearing fruits.

The enclosed photographs show plants in their fourth growing season (third year of production).

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of apple tree, its flowers, foliage and fruit, as based on observations of specimens grown near Elne, South of France, with color in accordance with The R.H.S. Color Chart (Fourth Edition) provided by The Royal Horticultural Society of Great Britain.

The trees, flowers and fruits may vary in slight detail due to variations in soil type, cultural practices and climatic conditions.

The main characteristics of this new variety of semi-sweet apple are a small to very small fruit size with a color of skin considered orange red to red. The fruit flesh is white. The fruit is firm to very firm.

The time of beginning of flowering is medium whereas the time of beginning of fruit ripening is considered very late.

In comparison to its seed parent 'REGALYOU' apple tree variety (U.S. Plant Pat. No. 25,827), 'BABYLOVE' apple tree ripens later during the season. Namely, the fruits of 'BABYLOVE' apple tree variety are used to ripen in October, more particularly during the first two weeks of October according to the year, whereas fruits of 'REGALYOU' apple tree variety are used to ripen the last two weeks of September. Fruits are also different in regards of fruit size: 'BABYLOVE' fruit are considered to be small to very small whereas 'REGALYOU' fruit are considered to be large. The shape of 'BABYLOVE' fruit is considered to be small, round, and flatten whereas the shape of 'REGALYOU' fruit is considered to be obloid, round to slightly flatten. The over color of 'REGALYOU' fruit is considered orange red to red whereas for 'BABYLOVE' is considered bright red.

'Babylove' can be compared to a variety of apple tree named, 'PremA96', better known by its trademark name, 'Rockit'. The ROCKIT apple variety is obtained from a natural crossing between the apple tree named PACIFIC and the apple tree named GALA, whereas the new variety named BABYLOVE has been obtained through an open pollination of the apple variety named REGALYOU. The two varieties are different regarding their size and weight. The fruits of BABYLOVE are smaller than those produced by ROCKIT. Indeed, the fruit weight for the variety BABYLOVE is approximately 70 grams whereas the fruit weight for the variety ROCKIT is usually between 80 and 90 grams. The fruits of the ROCKIT variety show a diameter comprised between 5 to 6 centimeters, whereas the fruits of BABYLOVE are slightly smaller, with an average transversal diameter comprised between 5.2 and 5.5 centimeters. The fruits of the two varieties also slightly different regarding their main color; the fruit over color is orange red to red for BABYLOVE, and considered pink red for ROCKIT.

The following apple tree varieties are considered as good pollinators for the new variety 'BABYLOVE': 'REGALYOU' (U.S. Plant Pat. No. 25,827) and 'REGALSTAR' (U.S. Plant Pat. No. 26,766).

DETAILED DESCRIPTION

Referring more specifically to the pomological details of this new and distinct variety of apple tree, the following has been observed on trees in their fourth growing season (third year of production) under the ecological conditions prevailing at the orchards located near the town of Elne, Pyrénées-Orientales department, France.

All observations have been done on rootstock cultivar. The rootstock was a 'M9EMLA' (non-patented) tree. All major color code designations are by reference to The R.H.S. Color Chart (Fourth Edition) provided by The Royal Horticultural Society of Great Britain.

Tree:

Generally: The first year the apple tree is generally cut at 2.50 meters height. The length in one year for each lateral shoot varies from 0.60 meters to 0.80 meters. We are cutting the apple trees during the second year to a height of 2.50 meters. The form of the apple trees is cylindrical and the diameter is limited to 1 meter.

*Size.*—Medium to high as compared to other commercial apple cultivars. The tree size the first year was approximately 2.50 meters. The tree was pruned during each following dormant season to a height of approximately 2.50 meters. Current season's shoots growth could reach 0.80 meters. So, the tree size from the second year (second and next years) reached a final height of 3.10 to 3.30 meters with current seasons shoots length comprised.

*Spread.*—Approximately 1.0 meter with a cylindrical shape. The whole orchard was oriented to a central leader organization, with tree lines spaced of 4.0 meters and trees spaced of 1 meter in a same tree line.

*Vigor.*—Medium, tree growth reaches 0.60 to 0.80 meters the first growing season.

*Productivity*.—Good to very good productivity, every year and without alternation. The new variety produces adequate fruit set annually on a regular basis. The number of the fruit set varies with the prevailing climatic conditions and cultivar practices employed during the bloom period and is therefore not distinctive of the present variety.

*Bearer*.—Very regular every year.

*Type of bearing*.—On spurs and long shoots.

*Type*.—Ramified.

*Habit*.—Upright.

*Form*.—Naturally semi-spread.

*Hardiness*.—Hardy in all stone fruit growing areas of France and especially where the chilling requirement is between 700 and 1200 hours. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017, 1017 hours in 2017-2018, and 844 hours in 2018-2019 showed a good behavior of the tree in all cases.

*No injury with temperatures as low as* −12° *C. in winter*.—Good resistance to late frosts.

Trunk:

*Size*.—Medium. Approximately 35.0 to 40.0 millimeters ($4^{th}$ growing season) above 20.0 centimeters above the ground.

*Bark texture*.—Rough with lenticels.

*Lenticels*.—Small number of lenticels. The number of lenticels reaches 1 lenticel per $cm^2$.

*Lenticels size*.—Approximately 1.0 to 1.5 millimeters height and between 3.0 and 3.5 millimeters width ($4^{th}$ growing season).

*Lenticels color*.—Color of lenticels is considered beige (RHS Greyed Orange 164 D).

*Bark color*.—Brown (RHS Brown N200 B) to grey (RHS Grey 201 A).

Branches:

*Diameter*.—Branches at the 2nd growing season have an average diameter of 7.0 to 9.0 millimeters.

*Surface texture*.—Wood which is several years old has no furrowed appearance.

*Lenticels*.—Lenticels on mature branches are small with a diameter of about 0.5 to 1.0 millimeter and a round shape. The number of lenticels reaches on mature branches 5 lenticels per $cm^2$. The lenticel color is beige (RHS Greyed Orange 164 C or RHS Greyed Orange 164 D).

*Color*.—Branches are brown (RHS Grey Brown N199 A).

*Crotch angles*.—Approximately 75.0 degrees from the supporting branch. This particular characteristic is not considered distinctive of the variety, however.

*Internode*.—Generally from 21.0 to 25.0 millimeters length.

Current season shoots:

*Diameter*.—Average diameter from 5.0 to 6.0 millimeters.

*Surface texture*.—Rough, with approximately 5 lenticels per $cm^2$.

*Lenticels*.—Considered small with a diameter of about 0.5 to 1.0 millimeter and a round shape. The lenticel color is beige (RHS Greyed Orange 164 C or RHS Greyed Orange 164 D).

*Crotch angles*.—Approximately 65 degrees from the supporting branch. This particular characteristic is not considered distinctive of the variety, however.

*Internode*.—Generally from 17.0 millimeters to 22.0 millimeters length.

*Color*.—The color of current season shoots is considered brown (RHS Brown 200 A or RHS Brown 200 B) on lower part of shoots, and the color of the upper part is similar and colored in brown (RHS Brown 200 A or RHS Brown 200 B).

Bud scales:

*Size*.—Medium to large.

*Shape*.—Elongated and conic in shape.

*Surface texture*.—Pubescent.

*Color*.—The inside of the bud scales is yellow green (RHS Yellow Green 145 A) and the outside of the bud scales is purple brown (RHS Greyed Purple 183 A).

Leaves:

*Size*.—Small to medium for the species. The ratio leaf length/leaf width is 1.898.

*Length*.—The medium length is 85.0 to 90.0 millimeters without leaf petiole.

*Width*.—The medium width is 45.67 millimeters.

*Leaf form in transverse section*.—Concave.

*Leaf form*.—Entire.

*Apex*.—Attenuate.

*Base*.—Round-shaped.

*Margins*.—Slightly undulating.

*Margins shape*.—Bicrenate.

*Surface texture*.—No pubescence on lower surface of the leaves. No pubescence on upper surface.

*Thickness*.—Considered thick.

Leaf color:

*Upper leaf surface*.—Green (RHS Green 137 A).

*Lower surface*.—A lighter green (RHS Yellow Green 146 B) than the upper leaf surface color.

Leaf veins:

*Leaf venation*.—Pinnately veined.

Mid-vein:

*Width*.—Approximately 2.0 millimeters.

*Color*.—Light green (RHS Yellow Green 151 C) to purple (RHS Greyed Red 178 A), evolves with maturity.

Secondary veins:

*Color*.—Light green (RHS Yellow Green 151 C).

Leaf petioles:

*Size*.—Medium.

*Length*.—About 28.0 to 32.0 millimeters. The ratio between the leaf length and the petiole length is approximately 3.

*Diameter*.—About 2.0 to 2.5 millimeters.

*Color*.—Upper surface dark purple (RHS Greyed Purple 187 A). Lower surface purple (RHS Greyed Purple 183 A).

*Shape*.—Grooved.

Leaf stipules:

*Generally*.—No leaf stipules were observed.

Flowers:

Flower buds:

*Generally*.—At pre-floral stage of development, the floral bunches are made up with 5 to 6 floral buds having a conic shape with a round tip. Their form is evolving until blooming, with variables dimensions. Just before blooming, floral buds are approximately 8.0 to 10.0 millimeters in diameter and approximately 16.0 to 18.0 millimeters long.

*Distribution of flower buds*.—The distribution of the flower buds is considered homogenous on the trees.

*Color*.—This characteristic is dependent upon the proximity to bloom. At pre-floral stage of development, the bottom of the flowers buds, or calyx formed by sepals, or flower receptacle, the inner surface is of green color (RHS Yellow Green N144 A) and the outer surface is also considered green (RHS Yellow Green 147 C or RHS Yellow Green 147 D). The corolla formed by petals, is generally red to purple (RHS Greyed Purple 185 A or RHS Red Purple 60 A).

*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom*.—Generally early in April. The first bloom was observed from Apr. 13 until Apr. 21, 2016.

*Blooming time*.—Considered medium in relative comparison to other commercial apple cultivars grown in the Pyrénées-Orientales department, France. The date of bloom varies slightly with climatic conditions and cultural practices. Thus, the full bloom was observed from Apr. 13 until Apr. 21, 2016, and then from Mar. 29 until Apr. 9, 2017.

*Blooming period*.—Average 9 to 12 days. This characteristic varies slightly with the prevailing climatic conditions.

*Flower type*.—The variety is considered to have a showy type flower (rosette).

*Flower size*.—Considered large. Average diameter of the corolla is between 46.0 and 52.0 millimeters when totally opened.

*Bloom quantity*.—Between 120 and 150 flowers per meter.

*Flower bud frequency*.—Generally 5 to 6 flower buds appear per node.

*Fragrance*.—Medium.

Petal:

*Size*.—Considered medium to large for the species.

*Length*.—Generally between 28.0 and 31.0 millimeters.

*Width*.—Generally between 22.0 and 24.0 millimeters.

*Petal form*.—Round.

*Petal margins*.—Smooth to slightly undulating.

*Petal count*.—Usually 5.

*Arrangement of petals*.—Intermediate.

*Petal texture*.—Smooth.

*Petal color*.—White (RHS White N155 B) with violet pink spots (RHS Greyed Purple 186 A) on the outer surface of the petals.

*Fragrance*.—Soft.

Petal apex:

*Generally*.—The petal apices are generally wide dome shaped.

Petal claw:

*Form*.—The claw is considered to have a narrow form.

*Length*.—Approximately 2.0 to 3.0 millimeters.

*Width*.—Approximately 1.5 millimeters.

*Color*.—White (RHS WHITE N155 B), similar to the petal color.

Flower pedicel:

*Length*.—Average length between 18.0 to 23.0 millimeters.

*Diameter*.—Between 1.0 and 1.25 millimeters.

*Color*.—Green (RHS Yellow Green 146 B or RHS Yellow Green 146 C).

Calyx:

*Color*.—At the stage F of blooming, when the flower is open, the inner surface of the calyx, or flower receptacle, is of green color (RHS Yellow Green N144 A). The outer surface of the calyx is also considered green (RHS Yellow Green 147 C or RHS Yellow Green 147 D).

*Texture*.—The inner surface is smooth.

Sepals:

*Size*.—Usually considered medium.

*Length*.—Approximately 6.0 to 8.0 millimeters.

*Width*.—Approximately 4.0 to 5.0 millimeters.

*Number*.—Generally 5 sepals per flower.

*Sepal form*.—Conic.

*Margins*.—Smooth.

*Texture*.—The sepals show a thin pubescence.

*Color*.—Upper surface of the sepals is green (RHS Yellow Green 147 C) and slightly brown near the apex, and the lower surface is green (RHS Yellow Green 146 B).

Stamens:

*Average number of stamens per flower*.—Approximately 18 to 20 stamens per flower.

*Size*.—Variable in length, approximately between 10.0 and 12.0 millimeters in length, generally higher than pistil's length.

*Size compared to petals*.—The size of stamens is smaller than the size of petals.

*Color*.—Considered white (RHS Green White 157 B).

Pistil:

*Generally*.—The pistil is composed with carpels. The pistil is considered smaller than the stamens.

*Length*.—Approximately 9.0 to 11.0 millimeters long including the ovary, smaller than stamen's length.

*Color*.—Considered green (RHS Yellow Green 144 B to RHS Yellow Green 144 C).

Stigma:

*Diameter*.—Approximately 0.9 millimeter.

*Shape*.—Elliptic.

*Color*.—Light green (RHS Yellow Green 151 A).

Ovary:

*Length*.—Approximately 2.0 to 2.5 millimeters.

*Diameter*.—Approximately 2.0 to 2.5 millimeters.

*Texture*.—Pubescent.

*Color*.—Green (RHS Yellow Green 144 B).

Anthers:
*Size*.—Medium.
*Form*.—Cordate.
*Color*.—Considered Yellow (RHS Yellow 6 D).

Pollen:
*Generally*.—Pollen is abundant and stamens are fertile.
*Color*.—Pollen has a yellow color (RHS Yellow 11 A) which may evolve with maturity.

Fruits:
*Maturity when described*.—Firm to very firm at maturity.
*Date of first picking*.—Oct. 14, 2015, varies slightly with climatic conditions.
*Date of last picking*.—Oct. 2, 2017 varies slightly with climatic conditions. The harvest is generally performed in two runs.
*Ripening period*.—The ripening period is considered very late; it generally begins during the first two weeks of October. Last known picking times carry on from Oct. 14 to Oct. 18, 2015, then from Oct. 9 to Oct. 17, 2016, then from Oct. 2 to Oct. 11, 2017, then from Oct. 4 to Oct. 12, 2018 and then from Oct. 9 to Oct. 17, 2019.

Size:
*Generally*.—Considered small to very small ("baby apple"), with a homogeneous size between them.
*Average transversal diameter*.—About 52.0 to 55.0 millimeters.
*Average axial diameter*.—About 41.0 to 43.0 millimeters.
*Typical weight*.—Generally, between 70.0 grams. This characteristic is highly dependent upon the prevailing cultural practices, and therefore is not particularly distinctive of the variety.
*Position of the maximum diameter*.—At the middle of the fruit.

Fruit form:
*Generally*.—Round and slightly flattened, obloid.
*Fruit ribbing*.—Absent.
*Fruit suture*.—Absent.
*Form of the ventral surface*.—Smooth.
*Apex*.—Generally slightly depressed, non prominent.
*Base*.—Wide-mouthed, shallow.

Fruit stem:
*Generally*.—Considered short to medium.
*Length*.—Between 16.0 and 20.0 millimeters.
*Diameter*.—About 1.0 to 2.0 millimeters.
*Color*.—Greenish (RHS Yellow Green 152 A).

Stem cavity:
*Form*.—Shallow and semi-narrow.
*Depth*.—Average depth between 8.0 and 10.0 millimeters.
*Width*.—Between 11.0 and 14.0 millimeters.

Fruit eye basin:
*Form*.—Round.
*Depth*.—Average depth between 3.0 and 5.0 millimeters.
*Width*.—Between 9.0 and 11.0 millimeters.

Calyx:
*Generally*.—Symmetrical.
*Form*.—Closed.
*Pubescence*.—The calyx shows a thin pubescence.
*Size*.—Considered small. Approximately 4.0 millimeters.
*Calyx lobes*.—Generally, these lobes are not prominent on the fruit.
*Calyx tubes*.—Narrow, with the floral stamens in the tubes.
*Length of sepals*.—Between 3.0 and 4.0 millimeters.
*Position*.—In the middle.

Fruit skin:
*Thickness*.—Considered thin and strong.
*Texture*.—Smooth and glabrous.
*Tendency to crack*.—None.

Lenticels:
*Number*.—Medium. About 1 lenticel per $cm^2$ of fruit skin.
*Size*.—Small.
*Form*.—Round.
*Diameter*.—Approximately 1.0 millimeter.
*Color*.—White to light beige (RHS Yellow White 158 D).

Skin color:
*Over color*.—This over color is considered a luminous orange red (RHS Orange Red N34 A) to red (RHS Red 46 A) and covers 95% of fruit skin.
*Pattern of over color*.—Solid flush with weakly defined stripes.
*Ground color*.—The ground color is yellow orange (RHS Yellow Orange 18 A) and covers at the most 5% of the fruit skin.

Russeting:
*Russet around stem cavity*.—Very low.
*Russet on cheek*.—Absent or very weak.
*Russet around eye basin*.—Absent or very weak.

Flesh:
*Generally*.—Long shelf life after harvesting.
*Texture*.—Crunchy, melty.
*Fibers*.—No fibers.
*Firmness*.—Firm to very firm.
*Aroma*.—Present.
*Juice*.—Juicy at ripeness.
*Taste*.—Semi sweet, good to very good and aromatic.
*Brix*.—Superior to 12.0 degrees until 12.8 degrees. The medium Brix is 12.4 degrees and varies slightly with amount of fruit per tree and climatic conditions.
*Acidity*.—Medium.
*Color*.—White (RHS White 155 A) at ripening time.
*Aperture of locules in transverse section*.—Moderately open.
*Width of locules*.—Approximately 1.0 millimeter.
*Form of locules*.—Flattened.
*Vascular bundles*.—The number of vascular bundles is 10.

Fruit core:
*Form*.—Symmetrical.
*Position*.—At the middle of the fruit.
*Distinctness of core line*.—Distinct.
*Stamens*.—Visible.

Seeds:
*Count*.—Generally 8 seeds are present per fruit.
*Number of seeds per locule*.—Usually 4 to 5 seeds per locule.
*Size*.—Small to medium.
*Length*.—Approximately 6.0 millimeters.
*Width*.—Approximately 3.0 millimeters.
*Form*.—Ovoid.
*Texture*.—Smooth.

*Color*.—Considered dark Brown (RHS Greyed Orange 166 A) at ripeness.

Use: Dessert, fresh products, fruit juice.

*Market*.—Local and long distance. On the tree fruits can stay 10 days while keeping good gustative qualities. The lifetime after picking is also good.

Keeping quality: Good, held well for 3 to 4 months in cold storage at 1° C. and maintained good appearance and eating quality. At room temperature (18° C.), fruits are well preserved for about 2 months.

Shipping quality: Good, showed minimal bruising or scarring during picking, packing and shipping trials.

Plant/fruit disease resistance/susceptibility: In our growing conditions, no particular symptom was noticed. The 'BABYLOVE' apple tree seems to be not much sensitive to russeting or bitter pit, to apple withering, to rot, to Monilia or Oidium, to aphids, to leafhopper. The new variety also seems to be resistant to apple scab.

Robustness to winter: Very good for trees and flower buds.

Tolerance to dryness: Good.

The present new variety of apple tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of apple tree, substantially as illustrated and described, essentially characterized by its small to very small size which converts this variety in a very different kind of apple, and also characterized by its high yield and its round flattened shape, its orange red to red skin color, its firmness, and exceptional eating quality; the fruit is further characterized by its good handling and storage qualities.

* * * * *